United States Patent
Nolan et al.

(10) Patent No.: US 10,112,057 B2
(45) Date of Patent: Oct. 30, 2018

(54) NON-OCULAR PHOTO-BIOLOGICAL STIMULATION

(71) Applicant: KONINKLIJKE PHILIPS N.V., Eindhoven (NL)

(72) Inventors: Julian Charles Nolan, Pully (CH); Alexander Henricus Waltherus Van Eeuwijk, Eindhoven (NL); Hilbrand Vanden Wyngaert, Grobbendonk (BE); Yalin Ti, Shanghai (CN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 248 days.

(21) Appl. No.: 14/905,870

(22) PCT Filed: Jul. 11, 2014

(86) PCT No.: PCT/EP2014/064882
§ 371 (c)(1),
(2) Date: Jan. 18, 2016

(87) PCT Pub. No.: WO2015/010920
PCT Pub. Date: Jan. 29, 2015

(65) Prior Publication Data
US 2016/0158572 A1    Jun. 9, 2016

(30) Foreign Application Priority Data
Jul. 23, 2013  (EP) ..................... 13177538

(51) Int. Cl.
*A61N 5/06*     (2006.01)
(52) U.S. Cl.
CPC ......... *A61N 5/0603* (2013.01); *A61N 5/0618* (2013.01); *A61N 5/0622* (2013.01);
(Continued)

(58) Field of Classification Search
CPC .... A61N 2005/0605; A61N 2005/0618; A61N 2005/0622; A61N 2005/0648; A61N 2005/0626
(Continued)

(56) References Cited

U.S. PATENT DOCUMENTS 6,350,275 B1    2/2002  Vreman
2006/0064144 A1*  3/2006  Chen .................... A61N 5/0618
                                                    607/90

(Continued)

FOREIGN PATENT DOCUMENTS

CN    1432348    7/2003
EP    2550993    1/2013
(Continued)

OTHER PUBLICATIONS

PR Newswire, "A New Independent User Study Published: Bright Light Headset Benefits are Comparable to Those of Bright Light Lamps" (http://www.prnewswire.com/news-releases/a-new-independent-user-study-published-bright-light-headset-benefits-are-comparable-to-those-of-bright-light-lamps-179445141.html), Nov. 15, 2012.
(Continued)

*Primary Examiner* — Nathan J Jenness (57) ABSTRACT

A first light source is arranged to provide non-ocular photo-biological stimulation to a user via a first light emission. For example, the first light source may take the form of an in-ear light source arranged to provide the photo-biological stimulation via at least one ear canal of the user. A controller coordinates control of the first light emission with a second light emission provided by at least one second light source providing ocular stimulation to the user. The second light source may take the form of one or more luminaires arranged to illuminate an environment of the user via ambient light. In embodiments, the controller may be con-
(Continued)

figured to control the non-ocular light to counteract an effect on the user of the ambient light, or to enhance an effect of the ambient light.

3 Claims, 3 Drawing Sheets

(52) U.S. Cl.
CPC .............. *A61N 2005/0605* (2013.01); *A61N 2005/0626* (2013.01); *A61N 2005/0647* (2013.01); *A61N 2005/0648* (2013.01); *A61N 2005/0657* (2013.01); *A61N 2005/0663* (2013.01)

(58) Field of Classification Search
USPC ..................................................... 607/88–95
See application file for complete search history.

(56) References Cited

U.S. PATENT DOCUMENTS

| | | | |
|---|---|---|---|
| 2009/0326616 A1 | 12/2009 | Aarts | |
| 2012/0303099 A1* | 11/2012 | D'Ambrosio | A61N 5/0618 607/90 |
| 2012/0330387 A1* | 12/2012 | Ferraz Rigo | A61N 5/0618 607/90 |
| 2013/0274835 A1* | 10/2013 | Nissila | A61M 21/00 607/88 |
| 2014/0052220 A1* | 2/2014 | Pedersen | A61N 5/0618 607/88 |
| 2014/0277291 A1* | 9/2014 | Pugh | G02C 7/04 607/88 |

FOREIGN PATENT DOCUMENTS

| | | |
|---|---|---|
| JP | 2004041399 | 2/2004 |
| WO | 2008/029001 | 3/2008 |
| WO | 2010/078581 | 7/2010 |
| WO | 2010/140073 | 12/2010 |

OTHER PUBLICATIONS

PR Newswire, "Light-Responsive Melanopsin Found in Many Parts of the Human Brain" (http://www.prnewswire.com/news-releases/light-responsive-melanopsin-found-in-many-parts-of-the-human-brain-152310145.html), May 21, 2012.

Hatori, et al., "The Emerging Roles of Melanopsin in Behavioral Adaptation to Light", The Salk Institute for Biological studies, http://panda.salk.edu/pdf/emergingrolesofmopn4.pdf).

Phillips, et al., "Myopia, Light and Circadian Rhythms", Advances in Ophthalmology; Department of Optometry and Vision Science, The University of West Aukland, New Zealand, Mar. 2012.

Luvone et al., "Effects of Apomorphine, a Dopamine Receptor Agonist, on Ocular Refraction and Axial Elongation in a Primate Model of Myopia", Investigative Ophthalmology & Visual Science, vol. 32, No. 5, Apr. 1991).

Norton, et al., "Light Levels, refractive development, and myopia—A speculative review", Experimental Eye Research 2013, 1-10, Department of Vision Sciences, School of Optomometry, University of Alabama at Brimingham, USA, http:dx.doi.org/10.1016/j.exer.2013.05.004).

* cited by examiner

NON-OCULAR PHOTO-BIOLOGICAL STIMULATION

CROSS REFERENCE TO RELATED APPLICATIONS

This application is the U.S. National Phase application under 35 U.S.C. § 371 of International Application No. PCT/EP2014/064882, filed Jul. 11, 2014, published as WO 2015/010920 on Jan. 29, 2015, which claims the benefit of European Patent Application Number 13177538.9 filed Jul. 23, 2013. These applications are hereby incorporated by reference herein.

TECHNICAL FIELD OF THE INVENTION

The present disclosure relates to the control of non-ocular photo-biological stimulation, e.g. by means of illumination provided through the ear canal.

BACKGROUND OF THE INVENTION

Light-responsive melanopsin is found in many parts of the human brain. Melanopsin is a photopigment relevant to regulation of Circadian rhythms and other non-visual responses to light. It is most sensitive to blue light, but is also sensitive to other wavelengths of light in the visible spectrum.

WO 2008/029001 has disclosed that photo-sensitive intracranial nerve tissue can be stimulated via the ear canal. The in-ear light treatment makes use of bright light in the visible spectrum. The ear canal absorbs the light radiation, and radiation energy will be transmitted through the ear canal to regions of the intracranial nerve tissue containing melanopsin. Thus a biological effect can be created through visible-spectrum light which is provided in the ear canal. This has been substantiated through a number of recently published papers which include the following.

"A New Independent User Study Published: Bright Light Headset Benefits are Comparable to Those of Bright Light Lamps" (http://www.prnewswire.com/news-releases/a-new-independent-user-study-published-bright-light-headset-benefits-are-comparable-to-those-of-bright-light-lamps-179445141.html).

"Light-Responsive Melanopsin Found in Many Parts of the Human Brain" (http://www.prnewswire.com/news-releases/light-responsive-melanopsin-found-in-many-parts-of-the-human-brain-152310145.html).

"The Emerging Roles of Melanopsin in Behavioral Adaptation to Light (Megumi Hatori and Satchidananda Panda, The Salk Institute for Biological studies, http://panda.salk.edu/pdf/emergingrolesofmopn4.pdf).

The in-ear light treatment may also be integrated into a combined audio and light-emitting headset.

Further, EP 2,550,993 has disclosed that non-ocular light treatment can be provided not only through the ear canal, but also from other extracranial positions. These include positions below the "equatorial line" of the head formed by the cerebrum, from where light energy can reach regions located near the brain stem. This document also notes the presence of other photosensitive proteins which can be stimulated from such positions.

Non-ocular light treatment has been disclosed for treatment of various disorders including Seasonal Affective Disorder (SAD), migraines, anxiety, Obsessive Compulsive Disorder (OCD), and alcohol and nicotine addiction.

U.S. Pat. No. 6,350,275 B1 discloses a device for treating a circadian rhythm disorder in a subject. The device includes a plurality of light emitting diodes (LED's), preferably blue to green; a mounting to which the LED's are connected: a material for positioning the LED's within 3 cm of the subject, with an orientation toward the subject; a portable power supply electrically connected to the LED's; and a control connected to the LED's for altering the operation of the LED's.

SUMMARY OF THE INVENTION

It is also known that an ambience or mood experienced by a user may be varied according to the intensity and color of light seen by the user though the eye, such as ambient light in the user's environment. It is also known that non-image forming photoreceptors in the eye, such as the intrinsically photosensitive Retinal Ganglion Cells (ipRGC) or melanopsin-containing ganglion cells, play a major role in synchronizing circadian rhythms. A lighting atmosphere is primarily perceived via the vision system (rods, cones in the retina) and interpreted in the brain. The ipRGC are photosensitive cells (melanopsin being the photopigment) that do not contribute to the vision system but interact with other mechanism and pathways that for example regulate circadian processes in the body. For example, such effects may be exploited in conventional, ocular light therapy to treat disorders like Seasonal Affective Disorder (SAD).

Historically light treatments have been applied through the eye via ambient light and/or dedicated task light. Providing therapy through conventional lighting systems would not separate or distinguish between the visual effect of the provided light (e.g. the image forming function of light) and the non-visual effect of the provided light (e.g. non-image forming functions controlling circadian rhythms), as all the light produced would be perceived by the eyes.

In the present disclosure, treatment is provided through both ocular and non-ocular stimulation, wherein the ambient light and biological light received by a user may be split between two different sources of illumination. The ambient or other ocular light source may be provided by conventional means and detected by the eye, while a non-ocular light source may be provided for example by an LED and/or fiber optic and applied to the ear canal. Here it illuminates nearby photopigments such as melanopsin which creates the biological effect.

Today, non-ocular photo-biological light treatment and any ambient light that happens to be present in the user's environment are provided by separate, uncoordinated illumination sources. As such, there is no particular combined benefit. For example, users do not have the ability to individually tailor the non-ocular light stimulation in the context of an ambient light setting. Nor is there scope for any synergy between the effects of the ocular and non-ocular stimulation.

According to one aspect of the present disclosure on the other hand, there is provided a system comprises: a first light source arranged to provide non-ocular photo-biological stimulation to a user via a first light emission, and a controller configured to coordinate control of the first light emission with a second light emission provided by at least one second light source adapted to provide ambient or other ocular light stimulation to the user. The system comprises a second light source, wherein the second light source is arranged to provide ocular stimulation to the user via the second light emission, and the controller is configured to control the second light emission. The controller is configured to control the second light emission independently of the first light emission, and to control the first light emission in dependence on the control of the second light emission. For instance, the controller may control the lighting in a room shared amongst multiple users, and set a particular ambient light setting appropriate to the majority preference or joint working environment, e.g. an ambient lighting which is dim or with a yellow bias such as may be found in an air traffic control tower, aeroplane cabin or laboratory clean room, and which may have a subduing or calming effect on the users. If one particular user wishes to stay alert, the controller may receive a user preference or requirement and detect the fact that the current ambient light setting is contrary to that preference or requirement, and in response apply white, blue or blue-biased light to the ear canal to induce a sense of alertness to at least somewhat counteract the effect of the ambient light.

The first light source may comprise an in-ear light source arranged to provide the photo-bio logical stimulation via at least one ear canal of the user. Alternatively or additionally, the first light source may provide the non-ocular stimulation from one or more other extracranial positions. The second light source may provide the second light emission in the form of ambient light. The second light source may take the form of an artificial light source. For example, the second light source may comprise one or more luminaires arranged to illuminate an environment of the user via the second light emission. In such cases, the controller coordinates control of the first light emission with the perceived lighting atmosphere invoked by the second light emission. Alternatively or additionally, the second light source could comprise a directed light source such as specially adapted pair of glasses or goggles, or a visor, monocle, headset or headrest, arranged to provide light into one or both eyes of the user. However, an ocular light source positioned in close proximity to the eyes (within 3 cm), is positioned relative to and in close proximity to the subject and therefore does not invoke an ambient lighting atmosphere.

The ocular and non-ocular light emissions are preferably applied at the same time or overlapping in time. In embodiments, the coordination may comprise controlling one or both of the first light emission (providing the non-ocular stimulation) and second light emission (providing ocular stimulation) to counteract an effect of the other on the user. Alternatively, the coordination may comprise controlling one or both of the first light emission and the second light emission to enhance the effect of the other, or the controller may be operable to implement both of these two variants for use in different situations. The controller may be configured to control at least one of the first and second light emissions in dependence on the other.

The light applied via the second, non-ocular light source may additionally be controlled in accordance with a circadian rhythm of the user, e.g. to treat jetlag on aeroplanes the non-ocular light may be applied in response to determining that the cabin lighting has been set low but that the user's circadian rhythm is in a "daytime" phase.

In another embodiment, the controller may allow the user to select a particular combination of ocular and non-ocular light jointly under a single user option. For example the user may be presented with a set of discrete options such as "cosy and relaxed", "cosy and alert", "calm and alert" and/or "calm and relaxed". If the user selects the single option "cosy and alert" for instance, e.g. from an on-screen menu, then in response to the selection of that single option the controller both sets the second, ocular light source to a red or red-biased emission and the first, non-ocular light source to a blue or blue-biased setting.

In another embodiment, the system does not necessarily comprise the second light source and the controller is not necessarily arranged to control the second light source. Instead, the system may comprise a light sensor arranged to sense one or more properties of the second light emission from the second light source, and the controller may be configured to control the first light emission in dependence on the second light emission as sensed by the light sensor. E.g. the sensor may detect that the ambient light in an environment such as an aeroplane cabin, control tower or laboratory is dim or has a yellow bias, and in response the controller may apply white, blue or blue-biased light to the ear canal.

In yet another embodiment, the controller and first, non-ocular light source may be used to treat a disorder that is at least partially caused or exacerbated by lack of daylight, such as myopia. In this case, the second light source is the Sun and the second light emission is natural daylight. If the user is not being exposed to sufficient daylight or even any daylight at all, the controller may be configured to automatically coordinate with the unseen daylight by using a timer to automatically mimic a daily rhythm of the Sun, thereby stimulating the circadian cycle of the user.

According to a further aspect disclosed herein, there is provided a computer program product configured so as when executed on a computer-readable medium to perform operations in accordance with any of the above controller features.

BRIEF DESCRIPTION OF THE DRAWINGS

For a better understanding of the present disclosure and to show how embodiments may be put into effect, reference is made by way of example to the accompanying drawings in which.

DETAILED DESCRIPTION OF EMBODIMENTS

Figure 1:
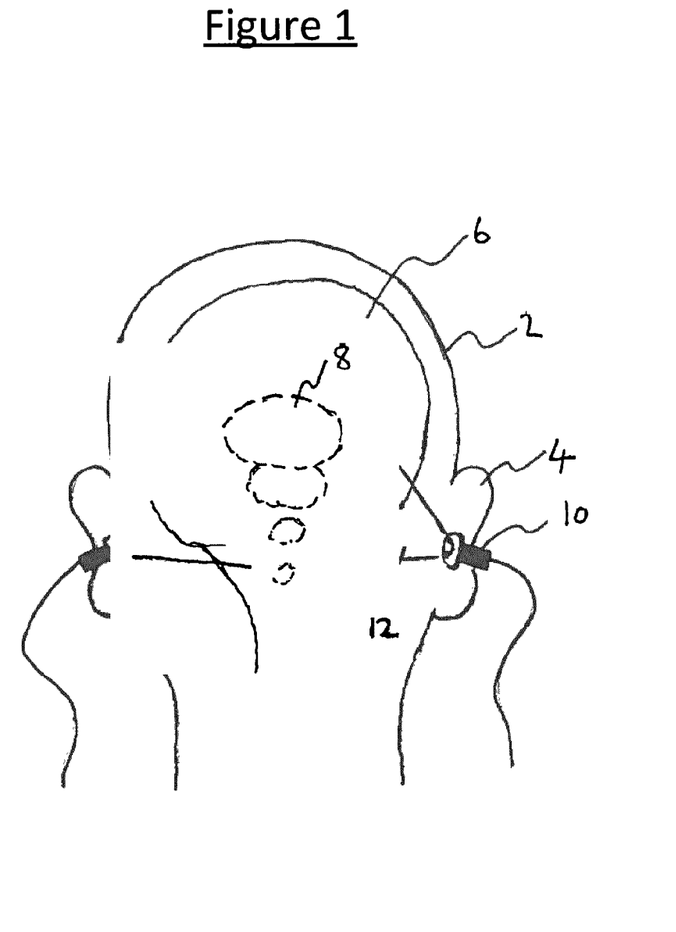
FIG. 1 is a schematic representation of a non-ocular light treatment.

FIG. 1 illustrates an example of non-ocular light treatment. The user 2 is a human or other invertebrate comprising a brain 6 and at least one ear 4 having an ear canal. The brain 6 has light sensitive regions 8. A first light source 10 is arranged to provide non-ocular photo-biological stimulation to one or more such regions through the application of visible-spectrum light 12. In embodiments this light may be applied through the ear canal, either by directly using a high efficiency LED or other lighting component, or indirectly where light from an LED or other lighting component is conducted to the ear by means of a fiber optic component. In embodiments, the first light source 10 may take the form of an in-ear light source comprising one or more in-ear lighting elements for insertion into one or more ear canals of the user 2. These may be referred to as "ear buds" and may be analogous in form to in-ear audio headphones (and in embodiments may also comprise one or more speakers configured to play music or other audio to the user 2).

The light emission 12 from the first light source 10 is incident on the surface of the ear canal and/or eardrum and radiation energy propagates to one or more of the light-sensitive regions 8, stimulating a biological response. The mechanism underpinning such photo-biological stimulation may be described as follows. Firstly, one or more light sensitive photopigments such as melanopsin exists in areas of the brain other than just the retina, which photopigments can be influenced by light introduced into the ear canal. Further, under light stimulation, melatonin can be generated and readily spreads into the cerebral fluid and blood due to it is lipophilic property, which is then responsible for the biological effect on the user 2.

Figure 2:
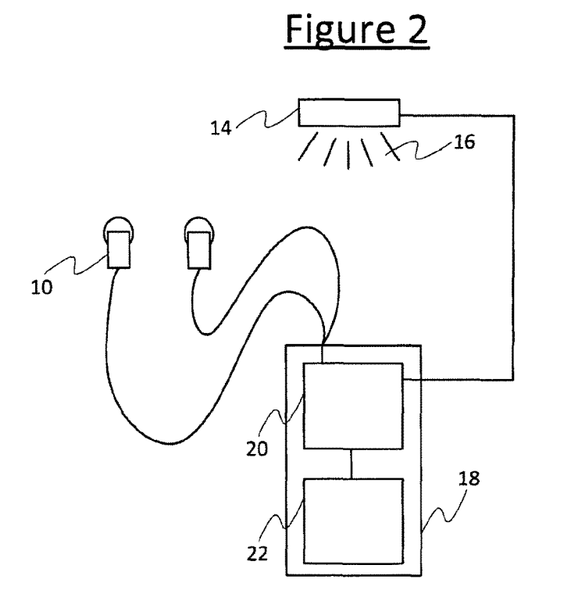
FIG. 2 is a schematic block diagram of a lighting system
Figure 3:
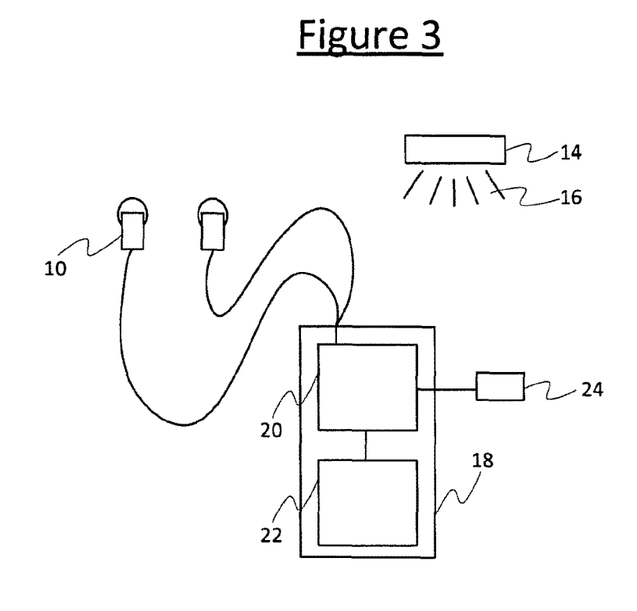
FIG. 3 is another schematic block diagram of a lighting system.

Referring to FIGS. 2 and 3, in addition to the non-ocular light 12, a second light contribution 16 flowing to the eye(s) of the user 2 is provided from a second light source 14 such as one or more luminaires, or dedicated illuminated glasses or goggles, or general purpose smart-glasses or goggles configured to generate light with specific properties. The second light source 14 could also take the form of a visor, monocle, headset, hat, booth, headrest or other arrangement for providing light into a user's eye or eyes. The example of ambient light provided from one or more luminaires will be referred to in the following.

The ambient light and non-ocular light received by a user are thus split, with two different sources of illumination being used to emit each respectively. Using this configuration the user may be exposed to ambient light in an environment such as a home or office with a desired lighting atmosphere. The non-ocular light does not disturb the ambience, and yet may be used to create biological effects which may for example differ from those usually associated with the perceived lighting atmosphere and yet which can still be related to that atmosphere.

A first embodiment is described in relation to FIG. 2. This illustrates a controlled light system for providing light to the eyes and to the ears comprising: a first light source 10 for emitting light 12 to at least one ear of a user 2; a second light source 14 for emitting light 16 to be received by at least one eye of the user 2; and a controller 18 for controlling the first and second light sources 10, 14 to generate light based on a required biological and emotional effect for the user 2. An alternative may be based on a required biological effect created by light provided through the ear and a functional effect created by light through the eye, an example of the latter being the vision function of office lighting. The controller 18 may be implemented in the form of a processor 20 comprising one or more processing units, and a memory 22 comprising one or more storage media such as magnetic or electronic storage, the processor 20 being arranged to execute code stored on the memory 22 which performs the control functionality. Alternatively the some or all of the functionality of the controller 18 could be implemented in dedicated hardware circuitry or re-configurable hardware such as an FPGA. Either way, the controller 18 may be implemented in any suitable unit or units, such as in a dedicated wall-mounted-unit with a wired or wireless connection to the light sources 10, 14, or in a dedicated or general-purpose portable unit with a wireless connection to the light sources 10, 14. In embodiments, the controller may be implemented as a wireless application to be run on a smart phone, tablet or laptop. In embodiments the functionality and components 20, 22 may be implemented on a single unit or split between multiple (remote) units, e.g. a user interface being implemented on the portable terminal while settings and/or preferences are stored on a server.

The idea disclosed is to provide an improved "brain" lighting system which can individually control the properties of light detected by photoreceptors associated with the eyes, with the ear canal and/or photoreceptors in other areas of the brain; such that a lighting atmosphere perceived by the eye may be created separately—but having an association or at least some degree of coordination with—a biological lighting effect detected by photopigments in areas of the brain other than the retinal area.

In embodiments, the time period during which the non-ocular light treatment is applied may be based on the circadian rhythm and application purpose. Short term effects can be used to influence concentration, alertness or enhance excitation. Longer term use may be required for circadian rhythm adjustment.

The system may be configured in a number of ways. For example red light may be displayed for the eyes (because people like the atmosphere) while at the same time blue light is applied to the ears (to keep the user alert). The light for the eyes may also be modulated based on the mood and preference of the user. In another example, a blue component may be added to the light observed by the eyes in order to further enhance the biological effect from the ears.

The idea may be used to achieve one or more of the following biological advantages. Firstly, based on light in the ears, biological controls can be applied in order to enhance concentration, alertness and/or excitation, preferably with at least a bias towards the blue end of the spectrum (430–480 nm). Secondly, there is less of a safety issue than with conventional light therapy, e.g. related to blue light hazard, as the delivery of the light is not via eyes. Thirdly, should it be required, the light treatment can be used for circadian rhythm modulation with consumer-specific periodic light dose delivery. Stimulation of dopamine release by bright light can also prevent myopia. Thus there may be a focus on lighting for health and wellbeing enhancement as well as mood.

Accordingly biological effects from applying light to the ears may include: treatment of SAD by enhanced blue part of spectrum, circadian rhythm adjustment (blue spectrum control), anti-aging (suppression of blue spectrum to maintain natural high melatonin level), and/or myopia control (through luminance).

These may be combined with the lighting atmosphere perceived by the eye. Warm colors such as red-orange, reds, yellows and yellow-greens can invoke an atmosphere that is radiant and cosy. For example red can be associated with a warm atmosphere and can stimulate arousal, appetites and conversation, while yellow can be associated cheerful atmosphere. Cool colors such as purples, blues and blue-greens can invoke an atmosphere that has a calming effect.

The system may be configured to operate in one or both of two different operating modes. In a first mode both the ambient and the in-ear illumination levels and characteristics are controlled by a single controller 18 and are dependent on each other. The memory 22 of the controller 18 stores a set of discrete options from which a user can select. Each option maps to a particular combination of settings: a particular setting for the ocular light and a particular associated setting for the non-ocular light. The ocular and non-ocular light settings are thus said to be dependent on each other in that they cannot be varied freely, but rather one is constrained to being set to a respective setting along with the corresponding setting of the other mapped to the same option. For each of the options, the respective associated ocular setting and its respective associated non-ocular setting will be stored together in association in the memory 22 in a respective entry of a data structure such as a look up table. For example the memory 22 may store a set of options as follows.

| Option: | Ambient Light Setting: | In-Ear Light Setting: |
| --- | --- | --- |
| "Cosy and alert" | Red bias | Blue bias |
| "Cool and alert" | Blue bias | Blue bias |
| "Calm and alert" | Green bias | Blue bias |
| "Calm and relaxed" | Green bias | Red bias |

The controller 18 is configured to allow the user to select from amongst the options, and to control the first light source 10 and second light source 14 accordingly to apply the respective pair of settings of the selected option. The options may for example be presented to the user in the form of a number of menu choices. In embodiments, the set of options may be preconfigured by a system designer, or the user may enter his or her preferences, e.g. into a smartphone based controller.

For example, a user may be using light treatment to make him or her feel more alert, but at the same time would like to work in an atmosphere which he or she feels is warm and cosy. The user therefore selects "cosy and alert". This may comprise a red biased ambient light level to create a short-term warm and cosy mood, combined with a blue biased in-ear light setting to create a longer term improvement in alertness. As a result the light outputs from the luminaire and in-ear illumination are balanced in terms of properties which include spectrum such that the longer term biological and shorter term emotional lighting effects desired the user can be achieved. As another example, for the setting "cool and alert", the in-ear light source would be set to a level such that the user's long term alertness could be maximized (e.g. by blue light) in the context of the ambient illumination already being provided by the luminaire 14 at its "cool" setting (which includes a strong blue spectrum bias).

In another example, the ambient light may be used to control short term mood or emotional effect, while the in-ear light may be used to provide a long term biological effect. A light treatment having a hormonal effect is longer lasting than any change in ambient light and mood setting captured directly via the visual system. Hence a long term effect may be considered as one having a biological effect that is substantially longer lasting than the duration of the light treatment creating the effect. For instance, a user may be undergoing a longer term light treatment such as a circadian rhythm treatment or SAD treatment via the in-ear lighting. However at the same time the user may be working in an environment with other ambient lighting requirements. E.g. say the user finds him or herself in a dim or red or yellow bias environment such as an aeroplane or clean room, but the SAD or circadian rhythm treatment is at such a stage that it requires bright white light. Conversely, the user may find him or herself in a brightly lit environment such as a joint office, but the SAD or circadian rhythm treatment is at a requiring red-bias light (like twilight or sunset, e.g. because the user has just arrived at the office in that country and is jetlagged). To accommodate these scenarios the controller 18 and memory 22 may be configured with a set of options each defining a pair of complementary settings such as: "aeroplane cabin, SAD daytime phase" (dim ambient with warm color temperature, bright white in-ear light); and "office, SAD twilight phase" (bright ambient, red bias in-ear light).

In a second mode, the ambient (e.g. short term mood or emotional effect) and in-ear light (e.g. long term biological effect) settings can be controlled individually, with the ambient light 16 being set independently while the in-ear light setting is controlled in dependence on the ambient light setting. In this case the controller 18 is configured to apply a setting to the ambient luminaire(s) 14 without being constrained by any setting of the in-ear light source(s) 10. For example this may be a user setting for the lights in a room, or an automatic setting set by the controller 18 in response to detecting certain conditions such as the amount of natural light already present. The controller 18 also sets the in-ear lighting 12 of the in-ear light source(s) 10 of one or more users. However, the in-ear lighting 12 is set in dependence on the setting applied to the ambient lighting 16. In embodiments, the controller 18 may be configured to automatically control the in-ear lighting 12 to compensate for an effect of the ambient lighting setting, or conversely to augment an effect of the ambient lighting setting.

For example in offices where multiple people are working the ambient lighting may be constant, but individual workers can individually address different needs for biological light based on their personal preferences, on the ambient light to which they are currently exposed, and/or on long term effects associated with their historical light exposure. In another example, in a clean room environment workers are exposed to a light with a strong bias towards the yellow end of the spectrum. In this instance workers can compensate for any unwanted biological effects of this day-long biological ocular light bias using in-ear lighting. In embodiments the in-ear settings may also be determined by a user's profile or preferences.

A second embodiment is described in relation to FIG. 3. Here the system is similar to that of FIG. 2 except that the controller 18 is arranged to control the first light source 10 but not necessarily the second light source 14. Instead, the controller 18 is coupled to a sensor 24 arranged to sense at least one property of the light 16 from the second light source 14, e.g. its intensity and/or information on its color or spectrum. In this case the second light source 14 could be any independent light source in the environment, e.g. one or more luminaires providing ambient illumination and being controlled from a separate controller or switch.

Like the first embodiment, the controller 18 controlling the first light source 10 is configured to control the light source to generate light 12 for non-ocular light stimulation based on a required biological effect for the user. However in the second embodiment it is configured to do this by using the sensor 24 to detect the light 16 emitted from the second light source 14, and computing the light 12 to be emitted from the first light source (e.g. in-ear light source) in dependence on this detection.

The second embodiment may be used to achieve any one or more of the effects or advantages associated with the non-ocular treatment described in relation to the first embodiment, e.g. treatment of SADs, or to counteract/enhance effects of the ambient lighting, etc.

The controller 18 may be configured to act as a perceived lighting atmosphere compensator. It determines one or more attributes of the actual ambient lighting atmosphere 16 using a light sensor such as a photocell or camera (e.g. as integrated into mobile device). The controller 18 also determines a desired lighting atmosphere or a desired biological effect, e.g. linked to user preference, music type, location and/or activity, etc. The controller 18 then calculates a difference between actual and desired light atmospheres or actual and desired biologic effects, determines the required attributes of the in-ear light emission 12 to complement the light atmosphere 16 perceived by the eye and varies one or more attributes of the in-ear illumination device 10 to approximate the desired light atmosphere and/or desired biological effect.

In one example use case, a user works in a clean room which is illuminated by a light with a strong yellow bias. The ambient lighting conditions are detected, and used to determine the settings for the in-ear biological lighting system 10. For example, it may be determined that the user requires two hours of in-ear blue light therapy to compensate the effects of the clean room lighting. In embodiments the controller may be implemented at least in part on a mobile terminal like a smart phone. The determined compensation level may be presented to the user via the smartphone, and the user then has an opportunity of varying this according to their personal preferences and needs.

Figure 4:
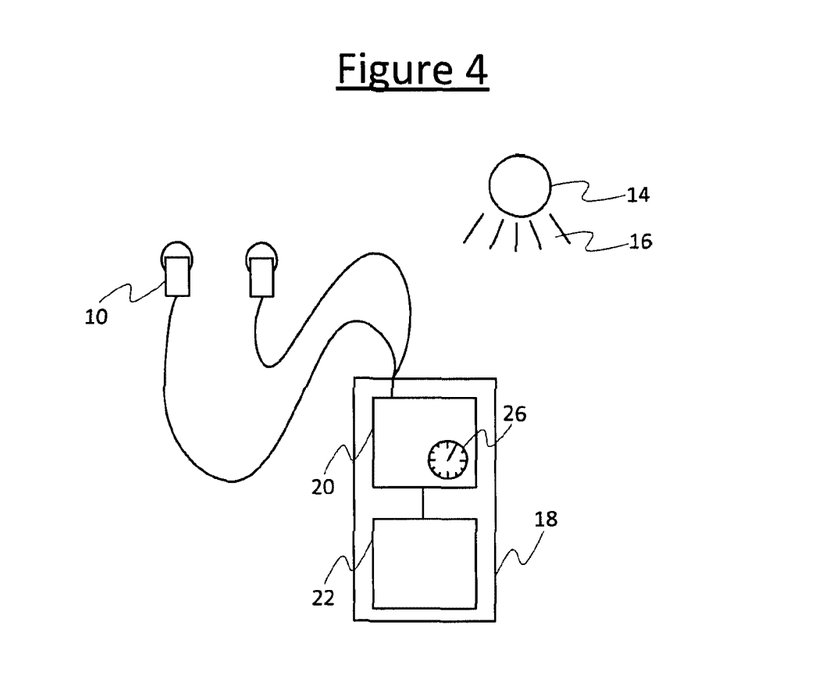
FIG. 4 is another schematic block diagram of a lighting system.

A third embodiment is now described in relation to FIG. 4. The third embodiment is similar to the second except that instead of a sensor 24 the controller 18 comprises a timer 26. Also, the second light source 14 in this example is not an artificial light source as in the first and second embodiment, but rather the sun. In this embodiment the user 2 may not necessarily have visibility of the second (natural) light source 14, e.g. because the user spends all or most of the day indoors. The controller 18 also need not have visibility of the light source 14 to which it is synchronizing. Instead, it coordinates the first light source 10 to the second light source 14 by using the timer 26 to synchronize to a periodic rhythm of the second light source, which for the sun is a daily rhythm.

For example the controller 18 may be programmed to automatically switch on and off at certain times each day, or to vary between such times, e.g. during the daytime or a certain window during the daytime when the user should otherwise be exposed to natural light. This can help stimulate the user's circadian rhythm even when deprived of a natural cycle, but without the need for harsh or inconvenient ocular treatment with bright light.

An example use case is to avoid after lunch drowsiness by providing supplemental blue light via the ear canal therewith not disturbing other users in a shared office environment and not requiring different ambient office lighting. As many users in open plan offices may already use in-ear headphones to provide their personal background music, this time-based, activity-based or calendar-based non-ocular light treatment can easily be implemented.

Another example use case is to treat myopia. Bright light stimulates dopamine release and can thereby prevent myopia. The intensity and wavelength of the light favor can stimulate increased retinal dopamine levels. For example see "Myopia, Light and Circadian Rhythms" (John R Philips, Simon Backhouse and Andrew V Collins; Advances in Ophthalmology; Department of Optometry and Vision Science, The University of West Aukland, New Zealand). See also CN 1,432,348.

There is also evidence to show that dopamine produced elsewhere than the retina can have an effect on myopia prevention. L-Dopa is a drug which increases dopamine concentrations, and this has been shown to inhibit myopic shifts occurring when a subject is deprived of light. See "Effects of Apomorphine, a Dopamine Receptor Agonist, on Ocular Refraction and Axial Elongation in a Primate Model of Myopia" (Michael Luvone et al, Investigative Ophthalmology & Visual Science, Vol. 32, No. 5, April 1991); and "Light Levels, refractive development, and myopia—A speculative review" (Thomas T Norton et al, Experimental Eye Research 2013, 1-10, Department of Vision Sciences, School of Optomometry, University of Alabama at Brimingham, USA, http:dx.doi.org/10.1016/j.exer.2013.05.004).

This indicates that an increase in dopamine levels can inhibit the progression of myopia regardless of whether the dopamine is produced via light stimulation through the eye. Thus light stimulation through the ear canal to produce dopamine can have a similarly positive effect on myopia as L-Dopa, but without the side effects.

Myopia can be a big problem in cities where children don't get outside enough. Researchers recommend two to three hours outside every day. Natural light varies between about 5,000-50,000 lux. Light that flickers (as opposed to being constant) can be even better for dopamine production and therefore very well suitable for non-ocular in-ear light stimulation. On the other hand, light can be bad for myopia if presented at the wrong time (out of sync with circadian rhythms).

A particular problem may occur where children need dopamine-enhancing light treatment to help prevent myopia, but they cannot be relied upon to action the treatment at the right times or, conversely, to not action treatment at bad times.

The third embodiment provides a solution by configuring the controller 18 to provide treatment to children and teenagers automatically under correct conditions only. The light-stimulation is automatically determined for a particular user and activated only at the correct time for the user (non-disruptive to circadian rhythms). This may additionally be based on a user light profile and requirement.

In embodiments, an in-ear light headset 10 may be integrated into earphones, e.g. with mp3 player attachment to create an mp3 player accessory to generate and control the light.

The system may provide regulated light stimulation, in accordance with circadian rhythms. The user logs in with biometrics or other login information such as touchscreen fingerprint. Based on this, the controller 18 is configured to determine an identity of the user, including age. It also incorporates a clock 26 to tell time of day. The controller 18 may for example determine the circadian cycle of user from genetic profile information or use average profile. When a child uses the mp3 player with associated light device and is in the "daytime" phase of his or her circadian cycle, the controller 18 operates the in-ear light source 10 to provide light treatment 12 through the ears. When the required stimulation duration is exceeded, the controller 18 turns off this light 10, 12. The controller 18 and light source 10 are configured to prevent the child from activating the in-ear light 12 manually.

Optionally, the controller 18 may determine a user's likely requirement for dopamine light stimulation from a time-dependent light profile and user age. If stimulation is required, the controller 18 determines optimal intensity and duration. If stimulation is deemed not required then the light will not be activated even if the child is using headphones whilst in "daytime" phase. The controller 18 may be configured to build up estimated user light profile based on location, computer usage patterns and outdoor activity, using sensor data—if available—to determine activity of the user and light exposure. The controller 18 may be configured to use sleep and/or waking data if available, e.g. from sleep apps or user's calendars, to determine circadian cycle. In embodiments the controller may apply flicker to the in-ear light 12 to create more benefit.

In yet further embodiments, the controller 18 may be configured to implement two or more of the first, second and third embodiments as different modes for use in different situations.

It will be appreciated that the above embodiments have been described only by way of example. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A system comprising:
   a first light source configured to provide non-ocular photo-biological stimulation to a user via a first light emission;
   a second, artificial light source configured to provide ocular stimulation to the user via a second light emission illuminating the user's environment, the second light emission being configured to invoke a lighting atmosphere capable of being perceived by an eye of the user;
   a controller configured to control the second light emission independently of the first light emission, and to control the first light emission in dependence on the control of the second light emission, wherein the controller is configured to control the first light emission to have a blue color or white color in response to detecting that the second light emission has a yellow color bias;
   wherein the controller is configured to receive a user preference, and wherein the controller is configured to control the first light emission in dependence on the user preference in response to the controller detecting that the second light emission is different from the user preference, so as to counteract an effect on the user different from the user preference by the ocular stimulation provided by the second light emission.

2. A system comprising:
   a non-ocular light source configured to provide non-ocular photo-biological stimulation to a user at a controllable intensity and spectrum via a non-ocular light emission;
   a light sensor configured to sense an ambient intensity and spectrum of an ambient light emission from an ambient light source;
   a controller configured to:
     receive a user preference light intensity and spectrum,
     receive the sensed ambient light intensity and spectrum,
     in response to the sensed ambient light intensity and spectrum differing from the received user preference light intensity spectrum, control the non-ocular light source in dependence on the sensed intensity and spectrum of the light emission to counteract the difference between the user preference and ambient light intensities and spectra, wherein the spectrum of the non-ocular light emission is biased blue when the user preference is to be alert and is biased red when the user preference is to relax.

3. A system comprising:
   a first light source configured to provide non-ocular photo-biological stimulation to a user via a first light emission;
   a second, artificial light source configured to provide ocular stimulation to the user via a second light emission illuminating the user's environment, the second light emission being configured to invoke a lighting atmosphere capable of being perceived by an eye of the user;
   a controller configured to control the second light emission independently of the first light emission, and to control the first light emission in dependence on the control of the second light emission, wherein the controller is configured to control an intensity and spectrum of the first and second light sources; and
   wherein the controller is configured to receive a user preference, and wherein the controller is configured to control the first light emission in dependence on the user preference in response to the controller detecting that the second light emission is different from the user preference, so as to counteract an effect on the user different from the user preference by the ocular stimulation provided by the second light emission.

* * * * *